United States Patent
Main et al.

(10) Patent No.: US 10,729,876 B2
(45) Date of Patent: Aug. 4, 2020

(54) SLEEPING ENVIRONMENT CONTROL SYSTEMS

(71) Applicant: XSENSOR Technology Corporation, Calgary (CA)

(72) Inventors: Ian Main, Calgary (CA); Mitchell Robert Knight, Calgary (CA)

(73) Assignee: XSENSOR Technology Corporation, Calgary, AB (CA)

( * ) Notice: Subject to any disclaimer, the term of this patent is extended or adjusted under 35 U.S.C. 154(b) by 238 days.

(21) Appl. No.: 15/798,043

(22) Filed: Oct. 30, 2017

(65) Prior Publication Data

US 2019/0126000 A1 May 2, 2019

(51) Int. Cl.
| | |
|---|---|
| *A61M 21/02* | (2006.01) |
| *A47C 21/04* | (2006.01) |
| *A47C 21/00* | (2006.01) |
| *F24F 5/00* | (2006.01) |
| *A61M 11/00* | (2006.01) |

(Continued)

(52) U.S. Cl.
CPC ........... *A61M 21/02* (2013.01); *A47C 21/003* (2013.01); *A47C 21/044* (2013.01); *F24F 5/00* (2013.01); *A61M 11/005* (2013.01); *A61M 16/0066* (2013.01); *A61M 16/16* (2013.01); *A61M 16/161* (2014.02); *A61M 2021/0027* (2013.01); *A61M 2021/0044* (2013.01); *A61M 2021/0083* (2013.01); *A61M 2205/0294* (2013.01); *A61M 2205/07* (2013.01); *A61M 2205/103* (2013.01); *A61M 2205/18* (2013.01); *A61M 2205/3306* (2013.01); *A61M 2205/3334* (2013.01); *A61M 2205/3368* (2013.01); *A61M 2205/3375* (2013.01); *A61M 2205/42* (2013.01); *A61M 2205/502* (2013.01); *A61M 2205/587* (2013.01); *A61M 2205/7545* (2013.01)

(58) Field of Classification Search
CPC ..... A61M 21/00–02; A61G 11/00–009; A47C 21/003; A47C 21/04–048
See application file for complete search history.

(56) References Cited

U.S. PATENT DOCUMENTS

| | | | |
|---|---|---|---|
| 2007/0023044 A1* | 2/2007 | Kwok | A61M 16/0057 128/204.23 |
| 2008/0223953 A1* | 9/2008 | Tomono | A01M 1/205 239/102.2 |

(Continued)

FOREIGN PATENT DOCUMENTS

WO WO-2012159744 A2 * 11/2012 ............. F21V 14/02

OTHER PUBLICATIONS

Google Translation of WO 2012/159744 A2 (Year: 2012).*

*Primary Examiner* — Thaddeus B Cox
(74) *Attorney, Agent, or Firm* — Fenwick & West LLP (57) ABSTRACT

Sleep environment control systems adjust sleep environments independently for individual users. A sleep environment control system delivers multiple environment adjustments via one opening to a user supported by a mattress. The environment adjustments include airflow, water vapor, light, and sound. The sleep environment control system can be placed in adjacent to the mattress thereby to deliver the environment adjustments to the user. The environment adjustments are delivered to the user in a localized fashion such that they do not disrupt other users. The sleep environment control system further generates the one or more environment adjustments.

21 Claims, 5 Drawing Sheets

(51) Int. Cl.
*A61M 21/00* (2006.01)
*A61M 16/00* (2006.01)
*A61M 16/16* (2006.01)

(56) References Cited

U.S. PATENT DOCUMENTS

2010/0030013 A1* 2/2010 Brunelle ............... A61M 21/00
                                                      600/27
2018/0177974 A1* 6/2018 LaPorte ................ A61M 21/02

* cited by examiner

SLEEPING ENVIRONMENT CONTROL SYSTEMS

BACKGROUND

1. Field of the Invention

This invention relates generally to adjusting a sleep environment, and more specifically, to systems that deliver different environment adjustments in a sleep environment.

2. Description of the Related Art

Sleep is important. Creating a great sleep environment is essential to a restful sleep. However, it is difficult to create a great sleep environment that provides the right temperature and humidity. People generally have different preferences over the sleep environment. For example, one individual prefers a colder environment whereas another may prefer a warmer environment. In addition, people have different schedules. Alarms intended to wake one up can be disruptive to another. Discomfort during sleep disrupts a restful sleep and affects a person's productivity, concentration, and health. There is always a need for systems that provide a better sleep environment.

SUMMARY OF THE DISCLOSURE

Described herein are sleep environment control systems that adjust sleep environments independently for individual users. A sleep environment control system delivers multiple environment adjustments to a user in a non-disruptive manner. The environment adjustments include airflow, water vapor, light, and sound. The sleep environment control system is configured to be placed in adjacent to a mattress thereby to deliver the environment adjustments to the user supported by the mattress. The sleep environment control system is configured such that it does not disrupt or obstruct the user when being placed in adjacent to the mattress. The environment adjustments are delivered to the user in a localized fashion. The environment adjustments delivered to one user do not disrupt another. As such, personalized sleep environment control is achieved. The local area is typically near the user's body such as the user's head. The sleep environment control system further generates the one or more environment adjustments.

An example sleep environment control system includes a base, a distribution head, and a conduit. The base provides a structural support to the environment control system. The distribution head distributes one or more environment adjustments to the user. The base and the distribution head together generate the one or more environment adjustments. The conduit delivers environment adjustments that are generated in the base to the distribution head.

BRIEF DESCRIPTION OF THE DRAWINGS

The invention has other advantages and features which will be more readily apparent from the following detailed description of the invention and the appended claims, when taken in conjunction with the accompanying drawings, in which:

Figure (FIG. 1 illustrates an example environment in which an example sleeping environment control system operates, according to one embodiment.

DETAILED DESCRIPTION OF THE DISCLOSURE

Figure 1:
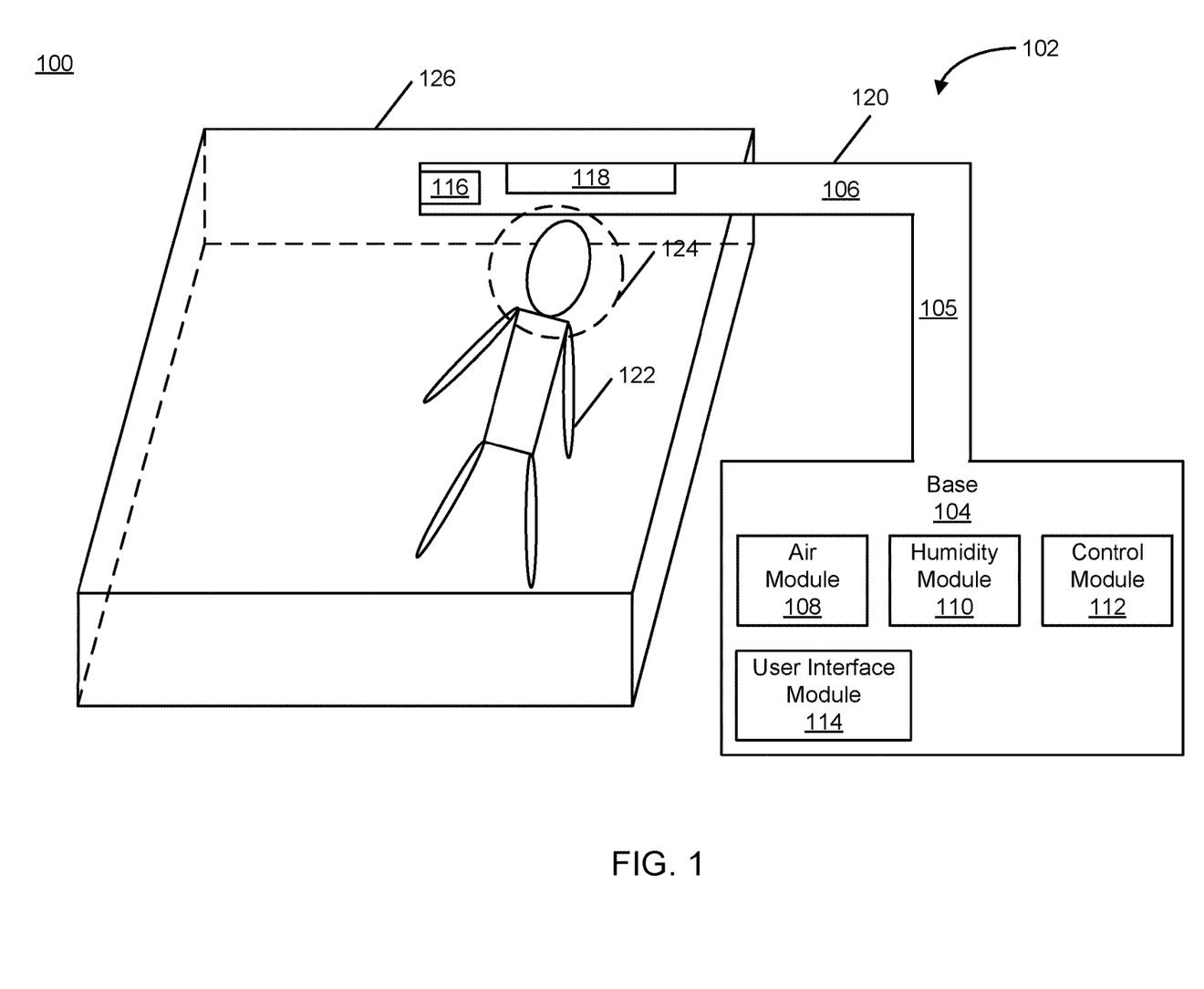

FIG. 1 illustrates an example environment 100 in which an example sleeping environment control system 102 operates, according to one embodiment. The sleeping environment control system is also referred to as the "control system." The control system 102 is positioned adjacent to a mattress 126 such that a distribution head 106 of the control system 102 is positioned above a local area 124. The local area 124 is typically in the vicinity of the body of an individual 122 supported by the mattress 126. For example, the local area 124 overlaps, surrounds, or is adjacent to a body part of the individual 122. The individual 122 can adjust the local area 124. The individual 122 adjusts a size of the local area 124 by adjusting a height of the distribution head 106 relative to a surface of the mattress 126. The environment control system 102 distributes one or more environment adjustments such as sound, air, water vapor, and light to the individual 122 via the distribution head 106. The one or more environment adjustments distributed by the environment control system 102 are of different modalities. An environment adjustment is distributed to the local area 124 in a localized fashion. That is, delivery of sound, air, water vapor, or light is focused in the local area 124. A degree of an environment adjustment outside the local area 124 that is distributed by the distribution head 106 is less than a threshold. For example, outside the local area 124, an amount of the airflow (or water vapor) distributed by the distribution head 106 is less than a threshold amount. Outside the local area 124, an intensity of the light distributed by the distribution head 106 is less than a threshold intensity. Outside the local area 124, a volume of the sound distributed by the distribution head 106 is less than a threshold volume. The threshold can be preconfigured or adjusted by the individual 122.

The environment control system 102 includes a base 104, the distribution head 106, and a conduit 105. The base 104 provides a structural support to the environment control system 102. The distribution head 106 distributes one or more environment adjustments to the individual 122. In the illustrated example, the base 104 and the distribution head 106 together generate the one or more environment adjustments. In other embodiments, the base 104 or the distribution head 106 generates the one or more environment adjustments. The conduit 105 delivers at least one environment adjustment generated in the base 104 to the distribution head 106.

The base 104 includes an airflow module 108, a vapor module 110, a control module 112, and a user interface module 114. The base 104 also includes a base housing (not shown) that encloses the airflow module 108, the vapor module 110, the control module 112, and the user interface module 114. The airflow module 108 generates purified airflow. The airflow module 108 includes a filter that purifies air and one or more fans that create the airflow. In some embodiments, the airflow module 108 includes a pair of fans facing each other. The pair of fans is parallel or substantially parallel to each other. A fan includes one or more high density fan blades to increase a static pressure. Using multiple fans generates a stronger airflow and lowers the noise level compared to using a single fan. The multiple fans can be positioned in parallel to each other. As further explained below with respect to FIG. 2, the pair of fans is affixed to the base housing such that the pair of fans is positioned perpendicular to the floor when the base 104 is positioned on the floor. The fans are typically positioned in the base 104 as far from the individual 122 as possible to substantially minimize the noise level. In some embodiments, the airflow module 108 includes a reflection plate positioned between the pair of fans. The reflection plate is positioned in the middle of the pair of fans and is parallel to the pair of fans. The reflection plate directs the airflow generated by the pair of fans in a direction towards the conduit 105. The reflection plate can also prevent the airflow created by separate fans from interfering. Furthermore, the reflection plate further reduces fan noise propagation by reflecting sound waves in a direction away from the conduit 105.

The vapor module 110 adjusts a humidity level in the airflow by outputting water vapor into the airflow generated by the airflow module 108. The vapor module 110 includes a piezoelectric transducer and a water tank, both of which are not shown. The piezoelectric transducer vaporizes water to generate water vapor. The size of the piezoelectric transducer is selected such that an amount of generated water vapor when mixed with the airflow at a maximum speed generated by the airflow module 108 produces an optimal humidity level. For example, the piezoelectric transducer is sized to maintain an airflow humidity at 40-50% RH (relative humidity) if the airflow module 108 outputs a maximum airflow (e.g., 258 $m^3$/h) in a 20% RH ambient environment. Water vapor in the airflow also lowers the temperature in the local area 124 and cools the individual 122. The vapor module 110 can generate water vapor continuously for a time period (e.g., 30 hours). In some embodiments, the vapor module 110 outputs water vapor into a transition section of the base housing where the water vapor is mixed with the airflow generated by the airflow module 108 before the moistened airflow enters the conduit 105. The vapor module 110 may further include a refill system to refill the water tank.

The control module 112 adjusts a degree of an environment adjustment according to a preferred setting thereby to adjust a local environment in the local area 124. The preferred setting can be preconfigured or configured by a user. The control module 112 can adjust the airflow module 108 to generate different levels of airflow, adjust the vapor module 110 to generate different levels of water vapor, adjust an audio module 116 to generate soundwaves of different wavelengths and magnitudes, and adjust a light module 118 to generate light of different wavelengths and intensities. For example, the control module 112 adjusts a fan speed of a fan included in the air module thereby to adjust a speed of airflow or an amount of airflow generated per unit time. As another example, the control module 112 adjusts the vibration of the piezoelectric transducer thereby to adjust an amount of water vapor generated per unit time. As a further example, the control module 112 adjusts a wavelength and/or an amplitude of the sound generated by the audio module 116. The sound generated by the audio module 116 can be used as alarms, entertainment, or sound masking. As yet another further example, the control module 112 adjusts a wavelength and/or an amplitude of the light generated by the lighting module 118. The light can be used to simulate a sunrise to awake the individual 122 or to provide a constant illumination. The control module 112 can also adjust a time point and a time interval of a particular environment adjustment.

Figure 6:
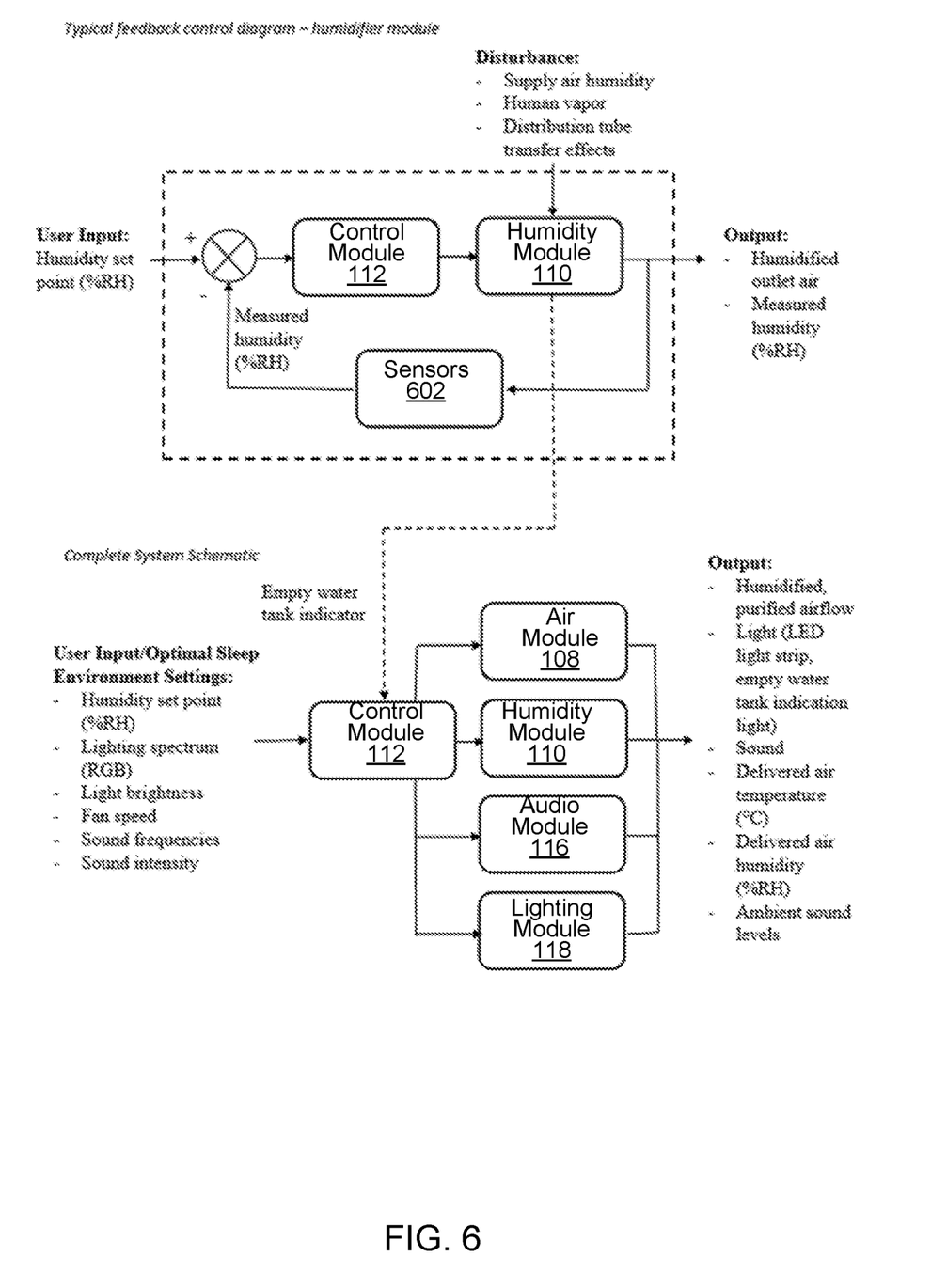
FIG. 6 illustrates an example control diagram, according to one embodiment.

In some embodiments, the control module 112 employs a feedback control. The control module 112 includes one or more sensors that measure the local environment in the local area 124. The one or more sensors are positioned in proximity to the local area 124 to accurately measure the local environment. For example, the one or more sensors are enclosed by the distribution head housing 120. The one or more sensors include a temperature sensor, a humidity sensor, a microphone, or a light sensor. The control module 112 adjusts the local environment based on a difference between the measured environment and the preferred setting. For example, if the measured temperature is higher than a preferred temperature, the control module 112 increases the level of the airflow and/or the humidity level. The control module 112 can also employ an open-loop control. For example, the control module 112 controls the airflow or lighting according to an airflow or light setting. FIG. 6 illustrates an example control diagram.

The user interface module 114 enables a user to interact with the control system. The user interface module 114 includes one or more user interface elements that allow users to provide user instructions. The user instructions may define a preferred environment setting. For example, a user can configure an alarm time, a preferred airflow level, a preferred humidity level, a preferred sound volume, a preferred alarm sound, a preferred light intensity, a preferred light color, and the like.

The housing is substantially cubically shaped. The housing includes an opening for coupling to the conduit 105. In some embodiments, the housing includes a cube and a transition section mounted to the cube. The cube includes an opening and the transition section overlaps the opening. The filter included in the airflow module 108 is mounted to the opening. The transition section is tapered conically shaped. The transition section includes an opening for coupling to the conduit 105. The transition section defines a space for mixing the airflow generated by the airflow module 108 and the water vapor generated by the vapor module 110. The transition section produces a static pressure and mitigates noise generated by the fans. In some embodiments, an interior surface of the housing includes a layer of sound absorbing materials for absorbing or substantially attenuating noise generated by other components of the airflow module 108.

The conduit 105 delivers one or more environment adjustments generated by the base 104 to the distribution head 106. The conduit 105 includes an elongated channel of which a cross-section is rectangular or circular shaped. As illustrated, the conduit 105 includes a first section 105a and a second section 105b. The second section 105b includes a vertical portion and a horizontal portion orthogonal to the vertical portion. The first section 105a is mounted to the base 104. The vertical portion of the second section 105b can slide relative to the first section 105a thereby to adjust a height of the horizontal portion of the second section 105b. The horizontal portion of the second section 105b secures the distribution head 106.

The distribution head 106 distributes one or more environment adjustments to the local area 124. The distribution head 106 includes a distribution head housing 120 that includes one opening (not shown) for distributing all environment adjustments. That is, the environment adjustments of different modalities are all distributed via the opening. The distribution head 106 further includes an audio module 116 and a lighting module 118. The distribution head housing 120 partially encloses the audio module 116 and the lighting module 118. The audio module 116 generates sound. The audio module 116 includes an electroacoustic transducer and one or more ethylene-propylene copolymer (EPOM) foam blocks for absorbing or reflecting soundwaves. The audio module 116 is positioned in the distribution head 106 such that the audio is outputted directionally to the individual 122. A location of the audio module 116 relative to the opening and/or a geometry of the opening can be adjusted to adjust a delivery of the sound to the individual 122. In the illustrated example, the audio module 116 is positioned at a distal end 123 of the distribution head 106. The lighting module 118 produces light. The lighting module 118 includes an array of LED (light emitting diode) assemblies that are mounted on an upper interior surface of the distribution head housing 120 opposite the opening. The opening is at least of a dimension such that light diffraction as it travels through the opening is minimal. The array of LED assemblies are spaced such that when they are lit, the light generated by the array of LED assemblies appears to be generated by a continuous light strip. In some embodiments, an interior surface of the distribution head housing 120 is coated with a low reflection coating to minimize or substantially minimize light reflection. The audio module 116 is designed to distribute sound in a region and to reduce propagation of sound outside the region. The lighting module 118 is designed in a similar manner. Details of the distribution head 106, the sound module 116, and the lighting module 118 are provided with respect to FIGS. 3 through 5B, respectively.

In some embodiments, the distribution head 106 rotates around a rotation axis 121 that is parallel to the ground. The environment control system 102 includes a stepper motor (not shown) to rotate the distribution head 106. The shaft of the stepper motor is geared and has cut teeth. The distribution head 106 also includes cut teeth reciprocal to those of the stepper motor shaft. A movement of the stepper motor shaft therefore can rotate the distribution head 106. As such, the opening in the distribution head housing 120 rotates around the rotation axis 121. The stepper motor module can be integrated with the distribution head 106. In addition, the distribution head 106 moves in a direction parallel to the ground. A location of the opening of the distribution head 106 can move in a direction parallel to the ground relative to the conduit 105. The distribution head 106 can slide relative to the horizontal portion of the second portion 105b. The distribution head 106 can also be rotated manually by a user.

Figure 2:
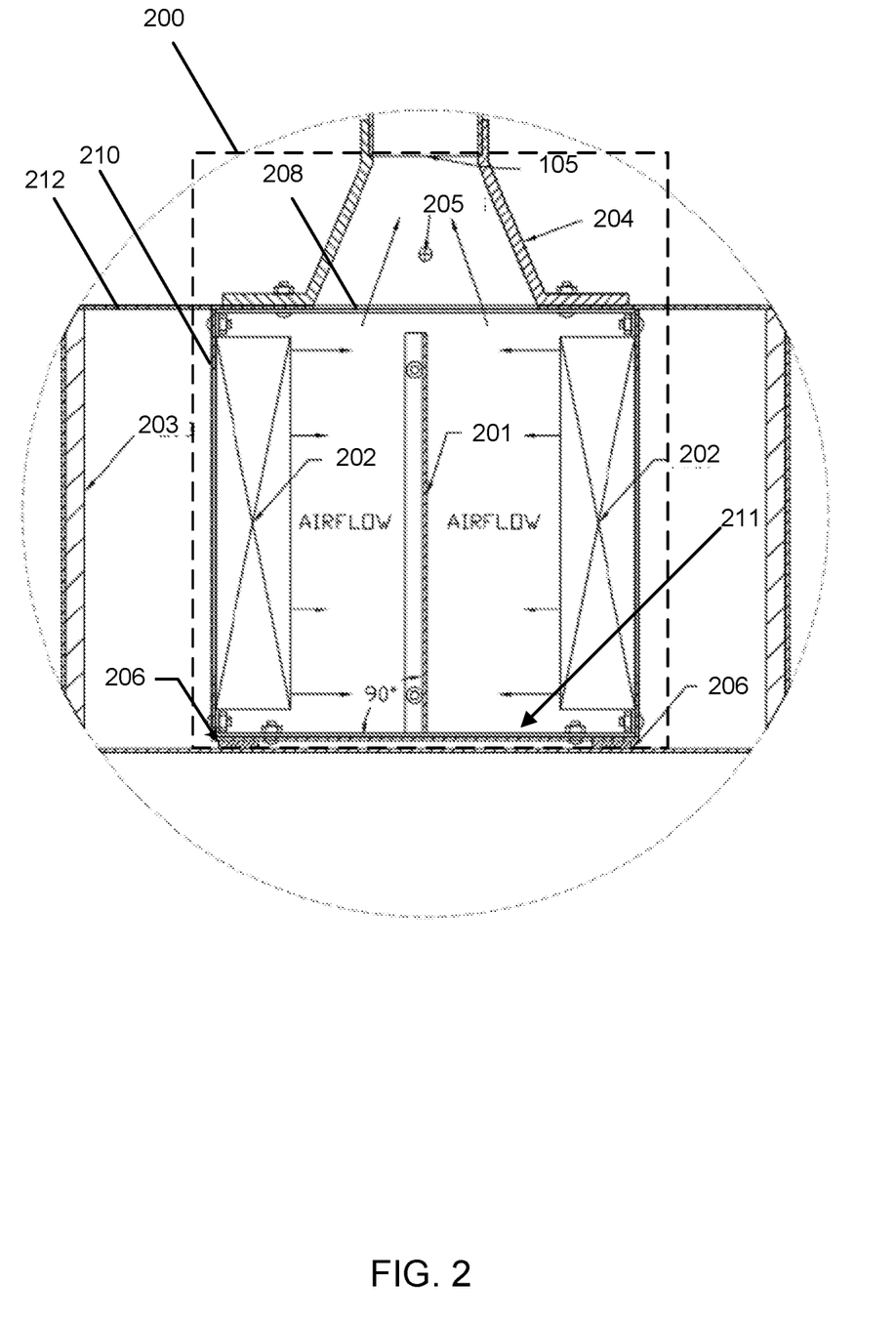
FIG. 2 is a cross-section view of an example base, according to one embodiment.

FIG. 2 is a cross-section view of an example base, according to one embodiment. The base includes a base housing that includes a cubical portion 212 and a transition section 213. The base housing encloses the air module 200. The air module 200 includes a pair of fans 202, a reflection plate 201, an air module housing 210, and an air filter 208. The air module housing 210 partially encloses the pair of fans 202 and the reflection plate 201. Within the air module housing 210, the pair of fans 202 is positioned such that one is positioned on one side and the other one is positioned on the opposite side of the air module housing 210. The pair of fans 202 faces each other. The reflection plate 201 is positioned in the middle between the pair of fans 202. The pair of fans 202 and the reflection plate 201 are positioned perpendicular to an interior surface 211 of the air module housing 210. The reflection plate 201 divides a chamber defined by the air module housing 210 into two chambers to reduce the interference between the airflow generates by the pair of fans 202. In addition, the reflection plate 201 reflects noise generated by the pair of fans 202 in a direction away from the conduit 105 thereby substantially preventing the noise from propagating through the conduit 105. The air module 200 also includes an enclosure liner 203 that absorbs sound waves reflected by the reflection plate 201. In the particular example, the enclosure liner 203 is applied to the interior surface of the cubical portion 212 of the base housing. In this way, the enclosure liner 203 absorbs noise generated by all components of the base 104. In addition, the air module housing 210 is supported by one or more damping members 206 that prevent the air module 200 from resonating. The one or more damping members 206 are made of a damping material.

The transition section 213 connects the rest of the base 200 to the conduit 105. The transition section 213 is mounted to the cubical portion 212 of the base housing. The transition section 213 defines a chamber for mixing airflow generated from the pair of fans. The vapor module 110 outputs water vapor into the chamber defined by the transition section 213 to be mixed with mixed with the airflow generated by the fans 202. The transition section 213 is tapered, which also reduces backpressure and flow generated noise. A narrower end of the transition section 213 is mounted to the conduit 105.

The filter 208 purifies the airflow by filtering out particles from the airflow. In the illustrated example, the air module housing 210 has an opening to allow airflow to pass and the filter 208 is positioned onto the air module housing 210 and overlaps the opening. The filter 208 can be positioned in other locations. For example, the filter 208 can be positioned within the transition section 213. As another example, the filter 208 can be positioned within the conduit 105. The filter 208 additionally attenuates or substantially removes the noise generated by the air module 200.

Figure 3:
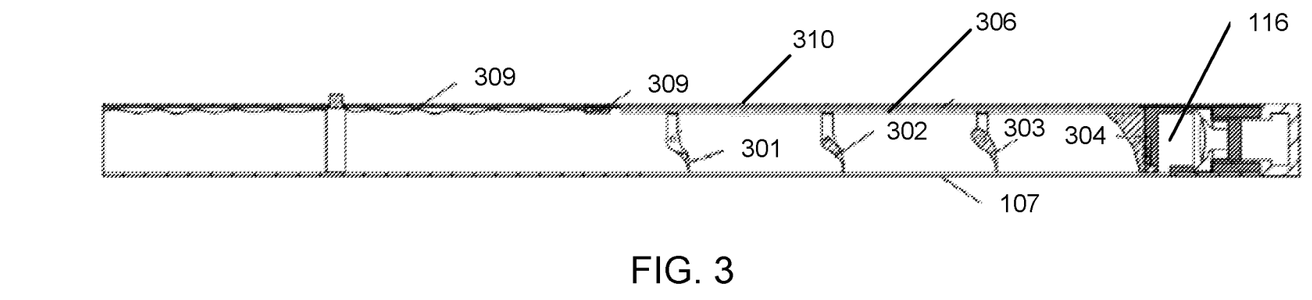
FIG. 3 is a cross-section view of an example distribution head, according to one embodiment.

FIG. 3 illustrates an example distribution head, according to one embodiment. The example distribution head includes vanes 301-304 and a distribution head housing 310 that includes an opening. The distribution head housing 310 encloses the vanes 301-304. The vanes 301-304 are each positioned to extend from an upper interior surface of the distribution head housing 310 to the opening that is opposite the upper interior surface. The vanes 301-304 divide the opening into multiple sections for distributing the environment adjustments. Each section can distribute a different amount of environment adjustment. The vanes 301-303 each have a still portion and a moving portion that rotates around a rotation center. A position of the moving portion of a vane 301-303 relative to the upper interior surface of the distribution head housing 310 can be adjusted by rotating the moving portion around the rotation centers. The rotation centers are separated from the upper interior surface by different distances. In one embodiment, the moving portion turns at a step size of a predetermined angle (e.g., 4°). The distribution head includes one or more handles (not shown) that allow a user to adjust the positions of the moving portions of the vanes 301-303. A handle (e.g., a tab) extends external to the distribute head housing 310. One handle allows a user to adjust positions of one or more vanes. The still portion of a vane 301-303 includes a clip that mounts the vane to the upper interior surface. The vane 304 is affixed within the distribution head housing 310 and its position relative to the interior surface of the distribution head housing 310 cannot be adjusted. In the illustrated example, the moving portions of the vanes 301-303 are airfoil-shaped and each have a leading edge and a trailing edge. The airfoil-shape reduces the flow separation around the turning vane and prevents areas of turbulence forming around the trailing edge. The vane 304 includes a sound absorbing backing to reduce sound reflections. This vane 304 prevents the airflow from entering the sound module 116. The vanes 301-304 are made of rigid materials such as polylactic acid or other plastics.

The positions of the vanes 301-303 can be adjusted to adjust a level of environment adjustment distributed to the local area. In particular, the positions can be adjusted separately. The amount of environment adjustment distributed through each different section of the opening can be adjusted separately as well. The vanes 301-304 can block light from propagation thereby to adjust an illumination level in the local area 124. In addition, the vanes 301-304 redirect the airflow in a direction to exit from the opening.

The distribution head housing 310 further encloses one or more cables 309 for transmitting electronical power or signals to and from the base 104. For example, the one or more cables 309 transmit electrical power from the base 104 to the audio module 116 or to the lighting module 118. As another example, the one or more cables 309 transmit electrical signals between the control module 112 and the audio module 116 or between the control module 112 and the lighting module 118. As a further example, the one or more cables 309 transmit electrical signals between the one or more sensors and the control module 112. The one or more cables 309 are flexible. In some embodiments, the one or more cables 309 are retractable and thus can extend or contract if the position of the distribution head 106 is adjusted thereby to prevent any damage to the cables 309 as a result of adjustment in the position of the distribution head 106.

Figure 4:
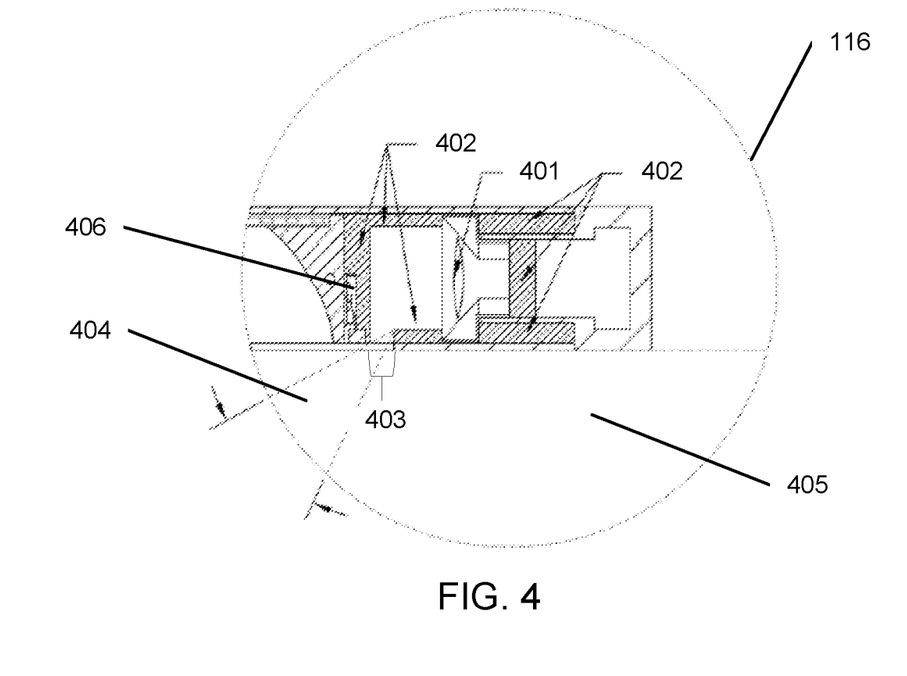
FIG. 4 illustrates a cross-section view of an end of an example audio module, according to one embodiment.

FIG. 4 illustrates a cross-section view of an example audio module, according to one embodiment. The example audio module 116 includes an electroacoustic transducer (i.e., a speaker) 401, one or more ethylene-propylene copolymer (EPOM) foam blocks 402 for absorbing soundwaves. The one or more EPOM foam blocks are positioned to define a region for soundwaves to propagate. For example, as illustrated, the EPOM foam blocks 402 are positioned to partially enclose the speaker 401 except for the region 403. The EPOM material minimizes sound reflection and reduces sound reverberation. The EPOM foam blocks 402 absorb soundwaves of different wavelengths at different rates. For example, the EPOM foam blocks 402 absorb soundwaves of higher frequencies at a higher rate than those of lower frequencies.

The region 403 is part of the opening and allows soundwaves to propagate. The soundwaves propagate through the region 403 continue to propagate in the region 404. The region 404 is the direct sound path of sound produced by the speaker 401. The speaker 401 outputs soundwaves in the 20-20,000 Hz frequency range. Sounds produced by the speaker 401 have the highest amplitude in the region 404 compared to neighboring regions. Preferably, the region 404 is overlaps the local region 124. A location and a size of the region 404 can be adjusted by an individual 122 to overlap the local region 124. For example, the individual 122 can adjust a position of the distribution head 106 relative to the mattress 126 such as a height and a distance to adjust the region 404. The individual 122 can also adjust a location of the speaker 401 relative to the opening thereby to adjust the region 404. In addition, a shape of the opening can be adjusted to adjust the region 404. In some embodiments, the region 404 is cone-shaped and has an aperture of 37 degrees.

Soundwaves also propagate in the region 405. For example, soundwaves produced by the speaker 401 can propagate through the distribution head housing 120, be reflected by different objects in the sleeping environment during propagation, or diffract when propagating through the opening 403. A magnitude of soundwaves propagated in the region 405 is correlated to the wavelengths of the soundwaves produced by the speaker 401. Soundwaves of lower frequencies (longer wavelengths) are more likely to appear in the region 405 than soundwaves of higher frequencies (shorter wavelengths).

In the illustrated example, the sound module 116 includes a microphone 406 to detect a sound level in the local area. The detected sound level can be used to adjust the output of the speaker 401 as provided above with respect to FIG. 1.

Figure 5A:
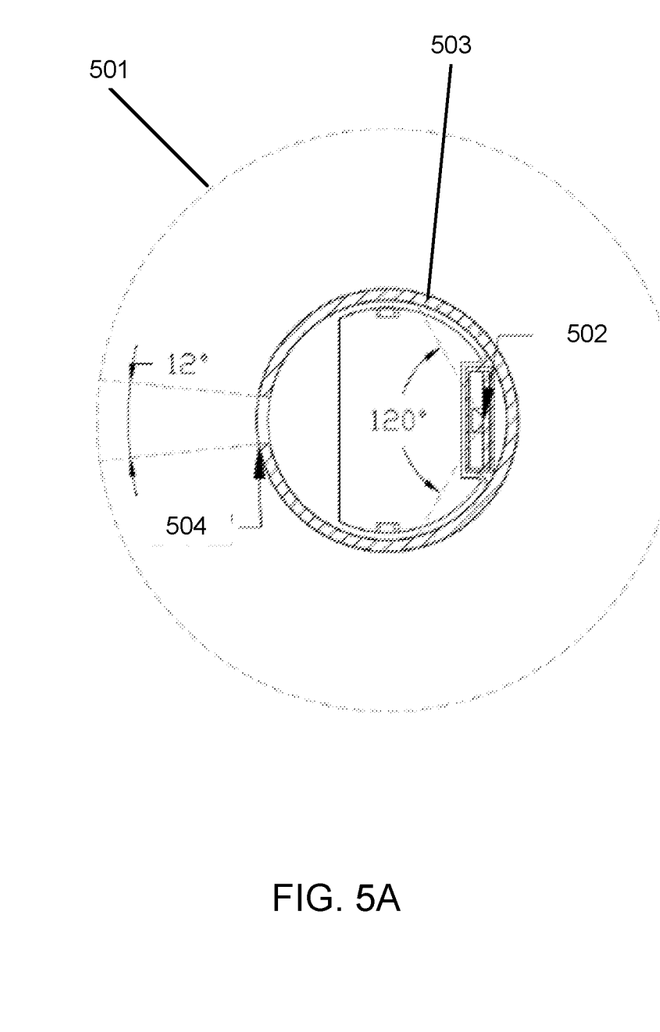
FIG. 5A illustrates a cross-section view of an example LED assembly, according to one embodiment.

FIG. 5A illustrates a cross-section view of an example LED assembly 501, according to one embodiment. An individual LED assembly 501 includes an LED 502 and an LED mount 503. The LED mount 503 secures the LED 502 to the distribution head housing 120. The LED 502 emits light of a particular beam angle (e.g., 120 degrees.) The LED mount 503 includes an opening 504 that allows light emitted by the LED 502 to pass. The opening 504 also distributes air, water vapor, and sound. The LED assembly 501 generates a light beam of a beam angle that is determined by the opening 504. The opening 504 can be adjusted such that the beam angle of the light beam generated by the LED assembly 501 is within a predetermined range (e.g., 12-120 degrees.) In some embodiments, an interior surface of the LED mount 503 is coated with a low reflection coating to minimize or substantially minimize light reflection.

Figure 5B:
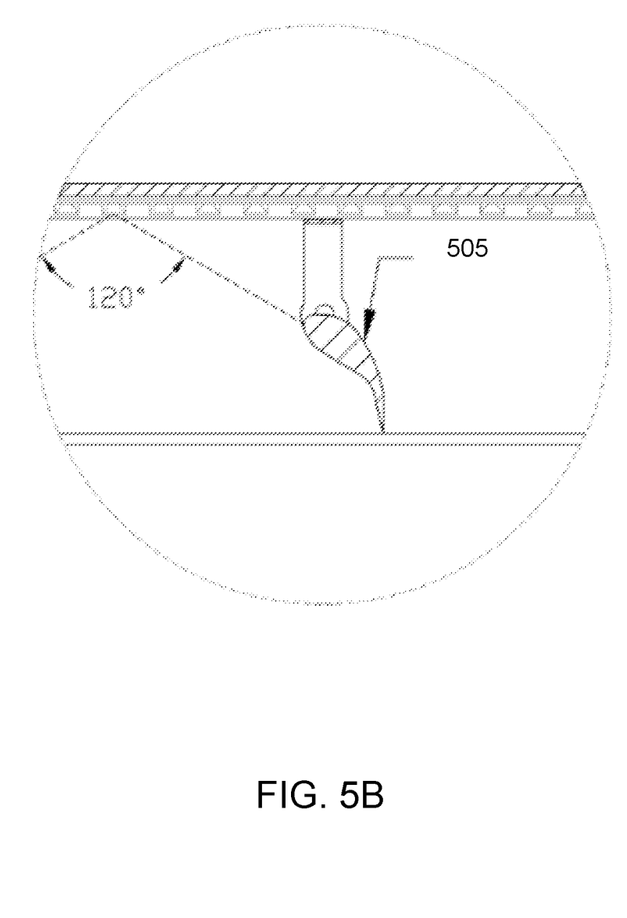
FIG. 5B is a cross-section view of a portion of an example distribution head, according to one embodiment.

An array of LED assemblies is used to provide adequate brightness for reading and have sufficient density to appear as a continuous light strip. The array of LED assemblies can output a rectangular-shaped light beam. The LED assemblies are evenly spaced within the distribution head housing 120. In some embodiments, two neighboring LED assemblies are separated by a center-to-center spacing of 6 mm. The vanes of the distribution head housing 120 can be adjusted to regulate a size as well as a shape of the light beam generated by the array of LED assemblies. As illustrated in FIG. 5B, adjusting a position of the vane 505 can adjust a size of a light dispersion area of the light emitted by the LED assembly 506. Smaller light dispersion areas are desired to prevent disruption on other users when there is less space between users, for example, in smaller beds.

The systems described herein can also be used in non-sleeping environments such as office environments, airplane cabin environments, cinema environments, cinema-like environments, and the like.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. An environment control system, comprising:
   a distribution head comprising a distribution head housing, the distribution head housing including an opening for distributing at least two environment adjustments to a local area, the at least two environment adjustments including sound and at least one of airflow, water vapor, or light;
   a first module for generating a first environment adjustment; and
   a second module for generating sound adjustment, the second module being a sound module that comprises a speaker and one or more ethylene-propylene copolymer (EPOM) foam blocks, the one or more EPOM foam blocks positioned to partially enclose the speaker;
   wherein a first degree of the first environment adjustment outside the local area is below a first threshold and wherein a volume of the sound outside the local area is below a second threshold.

2. The environment control system of claim 1, further comprising:
   a third module for generating a third environment adjustment.

3. The environment control system of claim 2, further comprising:
   a fourth module for generating a fourth environment adjustment.

4. The environment control system of claim 1, wherein the first module generates the light, and the distribution head housing partially encloses the first module.

5. The environment control system of claim 1, wherein the first module comprises an array of LED assemblies, the array of LED assemblies mounted to an interior surface of the distribution head housing opposite the opening.

6. The environment control system of claim 5, wherein an LED assembly comprises an LED and an LED mount, the LED mounted to the LED mount and the LED mount partially enclosing the LED.

7. The environment control system of claim 6, wherein the LED mount includes an opening that is adjustable.

8. The environment control system of claim 1, wherein the distribution head housing partially encloses the second module.

9. The environment control system of claim 1, wherein the one or more EPOM foam blocks are positioned to surround a section of the opening.

10. The environment control system of claim 1, wherein the second module further comprises a microphone to detect an ambient sound in the local area.

11. The environment control system of claim 1, wherein the first module comprises one or more fans to generate the airflow.

12. The environment control system of claim 11, wherein the first module comprises a reflection plate positioned between the one or more fans, the reflection plate to redirect the airflow into a conduit.

13. The environment control system of claim 1, further comprising a third module, wherein the third module comprises a piezoelectric transducer to generate water vapor.

14. The environment control system of claim 1, further comprising a third module, wherein the first module generates the airflow and the third module generates the water vapor, the environment control system further comprising a base housing enclosing the first module and the third module, the base housing including a transition section for mixing the airflow and the water vapor.

15. The environment control system of claim 1, wherein the distribution head includes one or more vanes enclosed by the distribution head housing, each of the one or more vanes extending from an interior surface of the distribution head housing to the opening opposite the interior surface, the one or more vanes including a vane having a moving portion that rotates around a rotation center.

16. An environment control system, comprising:
   a distribution head comprising a distribution head housing, the distribution head housing including an opening for distributing at least two environment adjustments to a local area, the at least two environment adjustments including at least two of airflow, water vapor, light, or sound;
   a first module for generating a first environment adjustment;
   a second module for generating a second environment adjustment, the second module enclosed by the distribution head housing;
   a base housing enclosing the first module; and
   a conduit coupled between the base housing and the distribution head housing, the distribution head housing slidable relative to the conduit in a direction parallel to a ground,
   wherein a first degree of the first environment adjustment outside the local area is below a first threshold and a second degree of the second environment adjustment outside the local area is below a second threshold.

17. The environment control system of claim 16, further comprising a control module to adjust the at least two environment adjustments according to a user instruction, the control module enclosed by the base housing.

18. The environment control system of claim 17, further comprising a set of sensors to measure an ambient environment in the local area, and the control module adjusts one environment adjustment based at least on the measured ambient environment.

19. The environment control system of claim 16, wherein the conduit includes a first section and a second section, the first section slidable relative to the second section in a direction perpendicular to the ground.

20. The environment control system of claim 16, further comprising a motor to rotate the distribution head housing around a rotation axis.

21. An environment control system, comprising:
   a distribution head comprising a distribution head housing, the distribution head housing including an opening for distributing at least two environment adjustments to a local area, the at least two environment adjustments including at least two of airflow, water vapor, light, or sound;
   a first module for generating a first environment adjustment;
   a second module for generating a second environment adjustment, the second module enclosed by the distribution head housing;
   a base housing enclosing the first module;
   a conduit coupled between the base housing and the distribution head housing; and
   a motor to rotate the distribution head housing around a rotational axis, wherein a first degree of the first environment adjustment outside the local area is below a first threshold and a second degree of the second environment adjustment outside the local area is below a second threshold.

\* \* \* \* \*